US009139848B2

(12) United States Patent
Velde

(10) Patent No.: US 9,139,848 B2
(45) Date of Patent: *Sep. 22, 2015

(54) ALFALFA VARIETY NAMED MAGNUM SALT

(71) Applicant: AGRIGENETICS, INC., Indianapolis, IN (US)

(72) Inventor: Michael John Velde, Clinton, WI (US)

(73) Assignee: Dow AgroSciences LLC, Indianapolis, IN (US)

( * ) Notice: Subject to any disclaimer, the term of this patent is extended or adjusted under 35 U.S.C. 154(b) by 105 days.

This patent is subject to a terminal disclaimer.

(21) Appl. No.: 13/787,213

(22) Filed: Mar. 6, 2013

(65) Prior Publication Data

US 2014/0033356 A1    Jan. 30, 2014

Related U.S. Application Data

(60) Provisional application No. 61/677,069, filed on Jul. 30, 2012.

(30) Foreign Application Priority Data

Jul. 30, 2012  (AU) ................................ 2012208997

(51) Int. Cl.
C12N 15/82 (2006.01)
A01H 5/00 (2006.01)
A01H 5/12 (2006.01)

(52) U.S. Cl.
CPC .............. *C12N 15/8289* (2013.01); *A01H 5/00* (2013.01); *A01H 5/12* (2013.01); *C12N 15/8245* (2013.01); *C12N 15/8247* (2013.01); *C12N 15/8274* (2013.01); *C12N 15/8281* (2013.01); *C12N 15/8286* (2013.01)

(58) Field of Classification Search
None
See application file for complete search history.

(56) References Cited

U.S. PATENT DOCUMENTS

| | | |
|---|---|---|
| 3,710,511 A | 1/1973 | Patterson |
| 3,861,709 A | 1/1975 | Mulcahy et al. |
| 4,535,060 A | 8/1985 | Comai |
| 4,654,465 A | 3/1987 | Brar et al. |
| 4,727,219 A | 2/1988 | Brar et al. |
| 4,769,061 A | 9/1988 | Comai |
| 4,940,835 A | 7/1990 | Shah et al. |
| 4,971,908 A | 11/1990 | Kishore et al. |
| 4,975,374 A | 12/1990 | Goodman et al. |
| 5,145,783 A | 9/1992 | Kishore et al. |
| 5,188,642 A | 2/1993 | Shah et al. |
| 5,188,960 A | 2/1993 | Payne et al. |
| 5,310,667 A | 5/1994 | Eichholtz et al. |
| 5,312,910 A | 5/1994 | Kishore et al. |
| 5,432,068 A | 7/1995 | Albertsen et al. |
| 5,463,175 A | 10/1995 | Barry et al. |
| 5,489,520 A | 2/1996 | Adams et al. |
| 5,491,288 A | 2/1996 | Chaubet et al. |
| 5,510,471 A | 4/1996 | Lebrun et al. |
| 5,550,318 A | 8/1996 | Adams et al. |
| 5,559,223 A | 9/1996 | Falco et al. |
| 5,561,236 A | 10/1996 | Leemans et al. |
| 5,633,435 A | 5/1997 | Barry et al. |
| 5,633,436 A | 5/1997 | Wandelt |
| 5,633,448 A | 5/1997 | Lebrun et al. |
| 5,646,024 A | 7/1997 | Leemans et al. |
| 5,648,477 A | 7/1997 | Leemans et al. |
| 5,689,052 A | 11/1997 | Brown et al. |
| 5,776,760 A | 7/1998 | Barry et al. |
| 5,804,425 A | 9/1998 | Barry et al. |
| 5,850,016 A | 12/1998 | Jung et al. |
| 5,866,775 A | 2/1999 | Eichholtz et al. |
| 5,874,265 A | 2/1999 | Adams et al. |
| 5,879,903 A | 3/1999 | Strauch et al. |
| 5,880,275 A | 3/1999 | Fischhoff et al. |
| 5,885,801 A | 3/1999 | Rao |
| 5,885,802 A | 3/1999 | Rao |
| 5,891,859 A | 4/1999 | Thomashow et al. |
| 5,892,009 A | 4/1999 | Thomashow et al. |
| 5,912,414 A | 6/1999 | Falco et al. |
| 5,919,675 A | 7/1999 | Adams et al. |
| 5,929,305 A | 7/1999 | Thomashow et al. |
| 5,939,599 A | 8/1999 | Chui et al. |
| 5,965,705 A | 10/1999 | Thomashow et al. |
| 5,969,213 A | 10/1999 | Adams et al. |
| 5,990,389 A | 11/1999 | Rao et al. |
| RE36,449 E | 12/1999 | Lebrun et al. |
| 6,005,165 A | 12/1999 | Dobrenz et al. |
| 6,040,497 A | 3/2000 | Spencer et al. |
| 6,063,947 A | 5/2000 | DeBonte et al. |
| 6,084,153 A | 7/2000 | Good et al. |
| 6,107,547 A | 8/2000 | Coruzzi et al. |
| 6,127,600 A | 10/2000 | Beach et al. |
| 6,130,366 A | 10/2000 | Herrera-Estrella et al. |
| 6,177,275 B1 | 1/2001 | Coruzzi et al. |
| 6,177,616 B1 | 1/2001 | Bartsch et al. |
| 6,194,638 B1 | 2/2001 | Dhugga et al. |
| 6,197,561 B1 | 3/2001 | Martino-Catt et al. |
| 6,225,114 B1 | 5/2001 | Eichholtz et al. |
| 6,232,529 B1 | 5/2001 | Singletary et al. |
| 6,248,876 B1 | 6/2001 | Barry et al. |
| RE37,287 E | 7/2001 | Lebrun et al. |
| 6,291,224 B1 | 9/2001 | Martino-Catt et al. |
| 6,307,126 B1 | 10/2001 | Harberd et al. |
| 6,323,392 B1 | 11/2001 | Charne |
| 6,338,961 B1 | 1/2002 | DeRose et al. |

(Continued)

OTHER PUBLICATIONS

Australian Patent Office Examination Report for Application No. 2012208997 dated Jun. 3, 2013 (5 pages).

*Primary Examiner* — Vinod Kumar
(74) *Attorney, Agent, or Firm* — Ronald S. Maciak; Michael Best & Friedrich LLP

(57) ABSTRACT

Disclosed is an alfalfa seed designated Magnum Salt and deposited as ATCC Accession Number PTA-13036. Also disclosed are plants, or parts thereof, grown from the seed of the cultivar, plants having the morphological and physiological characteristics of the Magnum Salt cultivar, and methods of using the plant or parts thereof in alfalfa breeding and alfalfa transformation.

22 Claims, No Drawings

(56) References Cited

U.S. PATENT DOCUMENTS

| | | |
|---|---|---|
| 6,346,403 B1 | 2/2002 | Rafalski et al. |
| 6,372,965 B1 | 4/2002 | Lightner et al. |
| 6,391,348 B1 | 5/2002 | Stilborn et al. |
| 6,399,859 B1 | 6/2002 | Nichols et al. |
| 6,417,428 B1 | 7/2002 | Thomashow et al. |
| 6,423,886 B1 | 7/2002 | Singletary et al. |
| 6,441,274 B1 | 8/2002 | Cahoon et al. |
| 6,459,019 B1 | 10/2002 | Falco et al. |
| 6,531,648 B1 | 3/2003 | Lanahan et al. |
| 6,566,587 B1 | 5/2003 | Lebrun et al. |
| 6,573,430 B1 | 6/2003 | Bradley et al. |
| 6,652,195 B2 | 11/2003 | Vickars et al. |
| 6,664,445 B1 | 12/2003 | Falco et al. |
| 6,664,446 B2 | 12/2003 | Heard et al. |
| 6,706,866 B1 | 3/2004 | Thomashow et al. |
| 6,713,663 B2 | 3/2004 | Weigel et al. |
| 6,717,034 B2 | 4/2004 | Jiang |
| 6,787,683 B1 | 9/2004 | Penna et al. |
| 6,794,560 B2 | 9/2004 | Harberd et al. |
| 6,801,104 B2 | 10/2004 | Zhu et al. |
| 6,803,498 B2 | 10/2004 | Dhugga et al. |
| 6,825,397 B1 | 11/2004 | Lowe et al. |
| 7,968,769 B2 * | 6/2011 | Velde .................. 800/298 |
| 2003/0009011 A1 | 1/2003 | Shi et al. |
| 2003/0079247 A1 | 4/2003 | Shi et al. |
| 2003/0150014 A1 | 8/2003 | Dhugga et al. |
| 2003/0163838 A1 | 8/2003 | Dhugga et al. |
| 2003/0166197 A1 | 9/2003 | Ecker et al. |
| 2003/0204870 A1 | 10/2003 | Allen et al. |
| 2004/0025203 A1 | 2/2004 | Singletary et al. |
| 2004/0034886 A1 | 2/2004 | Cahoon et al. |
| 2004/0068767 A1 | 4/2004 | Dhugga et al. |
| 2004/0078852 A1 | 4/2004 | Thomashow et al. |
| 2004/0098764 A1 | 5/2004 | Heard et al. |
| 2004/0128719 A1 | 7/2004 | Klee et al. |

* cited by examiner

ALFALFA VARIETY NAMED MAGNUM SALT

BACKGROUND OF THE INVENTION

Alfalfa (*Medicago sativa*) has often been referred to as the "Queen of Forages" because it is an excellent source of protein and digestible fiber, and because of its wide adaptation. Alfalfa has a high mineral content and contains at least 10 different vitamins and is an important source of vitamin A. Alfalfa improves soil tilth, and, in symbiosis with nitrogen fixing bacteria, is highly effective in converting atmospheric nitrogen to biological nitrogen. Thus, alfalfa is an ideal crop for use in crop rotation to improve soil tilth and replenish nutrients depleted from the soil by other crops such as corn.

The environment in which plants are grown for agricultural production continuously offers new obstacles to forage production, including, for example, high soil salinity. Development of stable, high yielding cultivars with superior characteristics is an ongoing goal of alfalfa breeders.

SUMMARY OF THE INVENTION

In one aspect, a *Medicago sativa* seed or cultivated alfalfa seed designated Magnum Salt and deposited under Accession Number PTA-13036 is provided.

In another aspect, a *Medicago sativa* alfalfa plant or cultivated alfalfa plant derived from the seed designated Magnum Salt and deposited under Accession Number PTA-13036 is provided. The plant may be grown directly from the seed such as deposited under Accession Number PTA-13036, or may be obtained indirectly from a plant grown directly from the seed by any suitable methods. For example, the plant may be generated from seed produced by a plant grown directly from the seed, from a cutting taken from a plant grown directly from the seed, or from tissue culture or callous derived from cells from a plant grown directly from the seed. In one embodiment, succeeding generations of plants derived from plants grown from the seed of Accession Number PTA-13036 are provided.

In another aspect, tissue culture of regenerable cells from a plant, or parts thereof, produced by growing seed deposited under Accession Number PTA-13036 and designated Magnum Salt and alfalfa plants regenerated from the tissue culture are provided.

In other aspects, the pollen and ovule of a plant derived from the seed deposited under Accession Number PTA-13036 is provided.

Also provided are methods for producing an alfalfa plant having an altered agronomic trait comprising introducing a polynucleotide into the alfalfa plant of claim 2, wherein the polynucleotide confers an altered agronomic trait selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

In another aspect, methods are provided for introducing a desired trait into alfalfa Magnum Salt. Alfalfa Magnum Salt plants are crossed with plants of a second alfalfa variety having the desired trait to produce F1 progeny plants, and F1 progeny plants are selected. The selected F1 progeny plants are backcrossed with alfalfa Magnum Salt plants and reselected for the desired trait and the physiological and morphological characteristics of alfalfa Magnum Salt three, four or more times in succession. Plants are produced that have the desired trait and the all the physiological and morphological characteristics of alfalfa variety Magnum Salt.

In another aspect, methods are provided for producing an alfalfa cultivar Magnum Salt-derived alfalfa plant by crossing Magnum Salt plants grown from Magnum Salt seed, representative seed of which has been deposited under ATCC Accession No: PTA-13036, with a second alfalfa plant to yield progeny alfalfa seed, and growing the progeny seed to yield an alfalfa cultivar Magnum Salt-derived alfalfa plant.

Other features and advantages of the invention will be apparent upon review of the specification.

DEFINITIONS

Terms used in the descriptions and tables that follow are defined as follows:

Flower color: Modern alfalfas are characterized by flower colors: purple, variegated, white, yellow and cream. Some cultivars are heterogeneous for flower color whereby some are predominately purple and variegated.

Forage yield is measured by harvesting herbage for part of or the entire life of the stand.

Fall dormancy: Alfalfa is classified into fall dormancy classes numbered 1 through 10, where dormancy group 1 is very dormant suited for cold climates and dormancy group 10 is very non-dormant and suited for very hot climates in which the plant would grow through out the winter months.

Winter survival: This evaluation is a prediction of the ability of the plant to persist over time.

Persistence: The ability of the cultivar to last over a minimum of two years. This measurement is documented in the visual percent stand remaining at the time of observation.

Anthracnose: Anthracnose is a serious stem and crown rot disease of alfalfa which can kill individual plants and cause rapid stand decline. Anthracnose is caused by *Colletotrichum trifolii*, a fungus which produces masses of tiny spores on infected stems and crowns. During periods of hot, rainy weather, spores are splashed from infected to healthy plants. Lesions develop on stems, causing stems to wilt and eventually die. The pathogen grows from stem tissue into the plant crown, and causes a crown rot which ultimately kills the plant.

*Aphanomyces* Root Rot: *Aphanomyces* root rot is caused by the fungal-like pathogen *Aphanomyces euteiches* causes death and poor growth of seedling alfalfa in slowly drained fields. It also can be a chronic disease of established plants that may result in significant yield reduction. *Aphanomyces* root rot is similar to and may occur in a complex with *Phytophthora* root rot and *Pythium* damping off, diseases which also occur in wet or slowly drained soils. Plants infected with *Aphanomyces* usually are stunted and chlorotic before they wilt and die, whereas *Phytophthora* and *Pythium* tend to kill seedlings quickly before plants become severely chlorotic.

Bacterial Wilt: The disease is caused by *Clavibacter michiganense* subsp. *insidiosum* (McCulloch) Davis et. al.=*Corynebacterium insidiosum* (McCulloch) Jensen. The bacterium survives in plant material in the soil, hay and seed for several years. It can be spread plant to plant via surface water (rain) irrigation and contaminated implement. Bacterial wilt is most common on plants growing in low, poorly drained areas of the field. It is also more common in wet years. Primary infection occurs when bacteria enter roots via wounds. Wounding can be caused by insect or nematode feeding, winter injury of mechanical injury. Once the bacterium enters the plant, symptoms are slow to develop, usually visible in the second or third crop year.

*Fusarium* Wilt: This disease is caused by *Fusarium oxysporum* f. sp. *Medicagines*. Wilting shoots are the first evidence of the disease. In early stages, the leaves may wilt during the day and regain turgidity at night. Bleaching of the leaves and stems follows, and a reddish tinge often develops in the leaves. Only one side of a plant may be affected at first, and after several months, the entire plant dies. Dark or reddish brown streaks occur in the roots appearing in cross section as small partial or complete rings.

*Phytophthora* Root Rot: *Phytophthora* root rot is caused by a soil-borne fungus, *Phytophthora medicaginis*, which is present in most alfalfa field soils. This fungus survives in organic debris and becomes active in wet soil. Water-saturated soils allow production of zoospores which have the capability to "swim" to roots and begin the infection process. Infection usually occurs on small lateral roots. From these initial infection points, the fungus gradually grows into the taproot. A yellow, red, or purple discoloration of leaves is the most characteristic above-ground symptom of *Phytophthora* root rot. Damage is most evident in low or poorly-drained areas of a field.

*Verticillium* Wilt: *Verticillium* wilt is caused by a fungus, *Verticillium albo-atrum*, which enters the water-conducting cells of the alfalfa plant and restricts the upward movement of water and nutrients. The fungus produces spores within the plant, or on cut stem surfaces following harvesting operations. Spores germinate on the cut surfaces and produce filaments (hyphae) that grow into stems and ultimately into roots. *Verticillium* wilt symptoms usually do not become conspicuous until the third production year. A yellow, V-shaped discoloration at the tip of a leaflet is an early indication of *Verticillium* infection. Eventually, leaflets wilt, turn yellow or pink, and often curl or twist. These abnormally small, twisted leaflets occurring near the top of the stem are the most characteristic symptoms of the disease. Stems are stunted, but frequently remain green and erect (in contrast to the drooping stems caused by anthracnose). Taproots appear healthy and sound, but have a dark ring (the water-conducting tissues) which is evident when the taproot is cut in cross section.

Pea Aphid: The long-legged pea aphid *Acyrthosiphon pisum* (Harris) adult is light to deep green with reddish eyes. It has a body length of 2.0 to 4.0 mm and most adults are wingless. The cornicles (a pair of tailpipe-like structures projecting from the abdomen) of this aphid are characteristically long and slender. The egg is approximately 0.85 mm long; the light green egg turns a shiny black before hatching. The nymph, the immature aphid is smaller than, but similar to, the larger wingless adult. It requires four molts to reach the adult stage. Pea aphids extract sap from the terminal leaves and stem of the host plant. Their feeding can result in deformation, wilting, or death of the host depending upon the infestation level. Plants that survive heavy infestations are short and bunchy with more lightly colored tops than those of healthy plants. Wilted plants appear as brownish spots in the field. Moreover, plants are often coated with shiny honeydew secreted by the aphids, and cast skins may give the leaves and ground a whitish appearance.

Stem Nematode: The stem nematode, *Ditylenchus dipsaci*, consists of microscopic worms approximately 1.5 mm long. The worms penetrate into plants from either the soil or infested planting material and occasionally from seeds. The female lays 250 eggs during a season and six generations may develop under optimum conditions when the temperature is in the range 15-20° C. As the number of nematodes increase, visual signs begin to occur. Leaves may curl, become yellow or die.

Northern Root-Knot Nematode: The northern root-rot nematode, *Meloidogyne hapla*, produces tiny galls on around 550 crop and weed species. They invade root tissue after birth. Females are able to lay up to 1,000 eggs at a time in a large egg mass. They are able to survive harsh winters, and persist in cold climates.

Southern Root-Knot Nematode: The southern root-rot nematode, *Meloidogyne incognita*, is a roundworm that infests at the roots of plants, where it deforms the normal root cells. The roots become gnarled and form galls.

DETAILED DESCRIPTION OF THE INVENTION

In one aspect, the present invention includes the seed of alfalfa cultivar Magnum Salt. A deposit of Magnum Salt seeds has been made under the Budapest Treaty and in accordance with 37 C.F.R. §§1.801-1.809 on Jul. 19, 2012 with the American Type Culture Collection (ATCC), 10801 University Boulevard, Manassas, Va. 20110. The deposited seed has been granted Accession Number PTA-13036. The deposit will be maintained in the depository for a period of 30 years, or 5 years after the last request, or for the effective life of the patent, whichever is longer, and will be replaced as necessary during that period. Seeds, plants or plant parts derived from the seed deposited as Accession Number PTA-13036 are provided.

By "a plant derived from the seed deposited as Accession Number PTA-13036", it is meant a plant that is grown directly from the seed deposited as Accession Number PTA-13036, or a plant that is obtained indirectly from a plant grown from the seed deposited as Accession Number PTA-13036. Plants obtained indirectly from a plant grown from the seed deposited as Accession Number PTA-13036 may be grown from a vegetative cutting, seed, callus or tissue culture obtained from a plant or plant part grown from the seed deposited as Accession Number PTA-13036 or a clonal plant thereof.

Magnum Salt is a 40 clone synthetic that expresses superior characteristics. Parent clones were selected out of saline soils for persistence, branch root and forage yield. The parent plants were progeny tested for one or more of the following traits: forage yield, stand persistence, resistance of bacterial wilt, *Fusarium* wilt, *Phytophthora* root rot, *Verticillium* wilt, anthracnose (Race 1), *Aphanomyces* root rot (Race 1), stem nematode, northern root-knot nematode, southern root-knot nematode and pea aphid.

The parent plants trace back to Dairyland Seed experimental plants. Parent plants were planted in field isolation and inter-pollinated by honey bees (*Apis mellifera*), leaf cutting bees (*Megachili rotundata*) and bumble bees (*Bombus impatiens*) near Sloughhouse, Calif. in 2008 to produce Syn. 1 as Breeder seed. Seed from parent plants were equally bulked each year to produce breeder seed.

Initial plants were selected for persistence in saline soils near Oriska, N. Dak. in 2004. Interpollination was carried out in plants grown in field isolation near Sloughhouse, Calif. in 2005. Plants were reselected in greenhouse saline soils for emergence and persistence in 2006. Interpollination was carried out in plants grown in field isolation near Sloughhouse, Calif. in 2007. Forage yield production under saline and control irrigation was evaluated at the University of Arizona and field evaluations were evaluated near Havana, N. Dak., Forman, N. Dak., in Buffalo, N. Dak. Breeder seed (Syn. 1) was produced by bulking seed of parent plants which were grown in field isolation near Sloughhouse, Calif. in 2008, or Breeder seed (Syn.2) was produced from Syn. 1. Foundation seed (Syn.2) was produced from Breeder seed and Certified seed (Syn. 2 or 3) from either Breeder or Foundation seed. Two generations of Breeder seed, one generation of Foundation seed and two generations of Certified seed classes are recognized. A maximum of three harvest years each is permitted on stands producing Breeder and Foundation seed with five years for Certified seed. Dairyland Seed will maintain sufficient Breeder seed for the projected life of the variety.

Provided is the use of a Magnum Salt plant, or part thereof, or an alfalfa plant having the physiological and morphological characteristics of the Magnum Salt plant, as a source of hay, haylage, greenchop and dehydration.

Magnum Salt was found to be highly resistant to bacterial wilt (*Clavibacter michiganense*), *Fusarium* wilt (*Fusarium oxysporum*), *Phytophthora* root rot (*Phytophthora megasperma*), *Verticillium* wilt (*Verticillium albo-atrum*), stem nematode (*Ditylenchus dipsaci*) and northern root-knot nematode (*Meloidogyne hapla*). Magnum Salt was found to be resistant to anthracnose (*Colletotrichum trifolii*) (Race 1), *Aphanomyces* root rot (Race 1) (*Aphanomyces euteiches*), pea aphid (*Acyrthosipon pisum*), and southern root-knot nematode (*Meloidogyne incognita*).

Magnum Salt is a moderately dormant variety similar to the fall dormancy 4 check. It expresses similar persistence to Magnum VI and 54V46 when grown in productive soil, such as near Clinton, Wis., and a 36% and 87% better persistence than Magnum VI and 54V46 respectively, when grown in saline soil such as near Buffalo, N. Dak. Magnum Salt is very winter hardy similar to the winter survival 2 check. Flower color in the Syn. 2 generation is 90% purple, 10% variegated with trace amounts of cream, white and yellow. Magnum Salt forage yield performance expresses a 5% advantage over 17 popular conventional varieties across 106 harvests. Its forage yield performance is 16% better than four popular ROUNDUP (RR) herbicide tolerant alfalfa varieties across 8 harvests.

The present invention contemplates using the Magnum Salt alfalfa plant, or part thereof, or an alfalfa plant having the physiological and morphological characteristics of the Magnum Salt alfalfa plant, as a source of breeding material for developing or producing an alfalfa plant in an alfalfa breeding program using plant breeding techniques. Plant breeding techniques useful in the developing or producing alfalfa plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature.

Methods are provided for introducing a desired trait into alfalfa Magnum Salt. Salt tolerance alfalfa plants are inter-mated to produce the next generation of seed. Seed from the first cycle, is re-selected, and inter-mated to produce the next generation of salt tolerant plants. This is process of selection and inter-mating is conducted until desired level of tolerance is achieved. Plants are produced that have the desired trait and the all the physiological and morphological characteristics of alfalfa variety Magnum Salt.

As used herein, the term "plant" includes, but is not limited to, plant cells, plant protoplasts, plant cell tissue cultures from which alfalfa plants can be regenerated, plant calli, plant clumps, and plant cells that are intact in plants or parts thereof "Plant part" includes, but is not limited to, embryos, pollen (pollen grains), ovules, seeds, flowers, pods, leaves, roots, root tips, anthers, and the like.

One may obtain alfalfa plants according to the present invention by directly by growing the seed Magnum Salt or by any other means. An alfalfa plant having all of the physiological and morphological characteristics of Magnum Salt can be obtained by any suitable methods, including, but not limited to, regenerating plants or plant parts from tissue culture or cuttings. The scope of the present invention is not limited by the method by which the plant is obtained.

The present invention contemplates genetic transformation of the Magnum Salt alfalfa plants. Polynucleotides may be introduced into a plant cell of alfalfa Magnum Salt to produce a transgenic Magnum Salt alfalfa plant. At least one, two, three, four, five, six, seven, eight, nine or ten polynucleotides may be introduced. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, whisker-mediated transformation, electroporation, sonication, microinjection, plant virus-mediated, and *Agrobacterium*-mediated transfer to the plant. Any suitable *Agrobacterium* strain, vector, or vector system for transforming the plant may be employed according to the present invention.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media.

In certain embodiments, the polynucleotides to be introduced into the plant are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

Promoters that may be used include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, ubiquitine, tCUP cryptic constitutive promoter, the Rsyn7 promoter, pathogen-inducible promoters, the maize In2-2 promoter, the tobacco PR-1a promoter, glucocorticoid-inducible promoters, and tetracycline-inducible and tetracycline-repressible promoters.

Polynucleotides may also be provided in a vector. Suitable vectors include plasmids and virus-derived vectors. Vectors known in the art that are suitable for transformation into plants, cloning, and protein expression may be used.

The present invention relates to transformed versions of the claimed alfalfa variety Magnum Salt as well as hybrid combinations thereof.

Polynucleotides that may be used include, but are not limited to, those that alter an agronomic trait such as conferring resistance to insects, disease, herbicides, or abiotic stress, or by altering fatty acid metabolism, carbohydrate metabolism, starch metabolism, amino acid metabolism, phosphorus metabolism, antioxidant metabolism, male sterility, site specific DNA integration, plant growth, forage yield and flowering. Examples of such traits are described in U.S. Pat. No. 6,652,195, the entire disclosure of which is herein incorporated by reference.

Polynucleotides that may be introduced include those that confer resistance to insects or disease, including, without limitation, coding sequences for plant disease resistance such as tomato Cf-9 for resistance to *Cladosporium fulvum*, tomato Pto for resistance to *Pseudomonas syringae* pv. Tomato, *Arabidopsis* RSP2 for resistance to *Pseudomonas syringae*, *Bacillus thuringiensis* (bt) protein, insect-specific hormones or pheromones and variants and mimetics, such as an ecdysteroid and juvenile hormones. Examples are described in U.S. Pat. Nos. 5,188,960; 5,689,052; and 5,880,275, the entire disclosures of which are each herein incorporated by reference. A plant resistant to a disease is one that is more resistant to a pathogen as compared to the wild type plant.

Polynucleotides that may be introduced include those that confer resistance to a herbicide, including, without limitation, coding sequences for mutant ALS and AHAS enzymes, coding sequences for glyphosate resistance imparted by mutant 5-enolpyruvl-3-phosphikimate synthase (EPSP), glyphosate N-acetyltransferase, glyphosate oxido-reductase and aroA; coding sequences for glufosinate resistance (phosphinothricin acetyl transferase (PAT) and *Streptomyces hygroscopicus* phosphinothricin acetyl transferase (bar); pyridinoxy or phenoxy proprionic acids and cycloshexones (ACCase inhibitor-encoding genes); triazine (psbA and gs+ genes); benzonitrile (nitrilase gene); coding sequences for acetohydroxy acid synthase; coding sequences for a chimeric protein of rat cytochrome P4507A1 and yeast NADPH-cytochrome P450 oxidoreductase; coding sequences for glutathione reductase and superoxide dismutase; coding sequences for various phosphotransferases; and coding sequences for modified protoporphyrinogen oxidase (protox). Examples are described in U.S. Pat. Nos. 4,975,374, 5,776,760, 5,463,175, 5,969,213, 5,489,520, 5,550,318, 5,874,265, 5,919,675, 5,561,236, 5,648,477, 5,646,024, 6,566,587, 6,338,961, 6,248,876 B1, 6,040,497, 5,969,213, 5,489,520, 5,550,318, 5,874,265, 5,919,675, 5,561,236, 5,648,477, 5,646,024, 6,177,616, 5,879,903, 5,804,425, 5,633,435, 5,145,783, 4,971,908, 5,312,910, 5,188,642, 4,940,835, 5,866,775, 6,225,114 B1, 6,130,366, 5,310,667, 4,535,060, 4,769,061, 5,633,448, 5,510,471, RE 36,449, RE 37,287, and 5,491,288, the entire disclosures of which are each herein incorporated by reference.

Polynucleotides that may be introduced include those that confer or contribute to an altered trait such as altered fatty acids, include, for example, coding sequences for stearoyl-ACP desaturase, FAD-2, FAD-3, LEC1, AGP, Dek1, Superal1, mi1ps, various Ipa genes such as Ipa1, Ipa3, hpt or hggt. Examples are described in U.S. Pat. Nos. 6,063,947; 6,323,392; 6,372,965, 6,423,886, 6,197,561, 6,825,397, and US Patent Publication Nos. 2003/0079247, 2003/0204870, the entire disclosures of which are each herein incorporated by reference.

Polynucleotides that may be introduced include those that confer or contribute to an altered trait such as altered phosphorus content, include, for example, coding sequences for a phytase, inositol kinase or for LPA alleles. Examples are described in U.S. Pat. Nos. 6,197,561, 6,291,224, 6,391,348, and US Patent Publication Nos. 2003/0009011, 2003/0079247, 2003/0079247, the entire disclosures of which are each herein incorporated by reference.

Polynucleotides that confer or contribute to an altered trait such as altered carbohydrate metabolism, include coding sequences for enzymes of starch and cellulose metabolism, such as thioredoxin, fructosyltransferase, levansucrase, alpha-amylase, invertase, starch branching enzyme, UDP-D-xylose 4-epimerase, cellulose synthases (CesA), UDP-glucose pyrophosphorylase, glycosyl transfersase, and glycosyl hydrolase. Examples are described in U.S. Pat. Nos. 6,531, 648, 6,232,529, 6,194,638, 6,803,498, 6,194,638, 6,399,859 and US Patent Publication Nos. 2003/0163838, 2003/0150014, 2004/0068767 and 2004/0025203, the entire disclosures of which are each herein incorporated by reference.

Polynucleotides that may be introduced include those that confer or contribute to an altered trait such as altered antioxidant content or composition, include, for example, coding sequences for a phyt1 prenyl transferase (ppt), or homogentisate geranyl geranyl transferase (hggt). Examples are described in U.S. Pat. Nos. 6,787,683, and US Patent Publication NO. 2004/0034886, the entire disclosures of which are each herein incorporated by reference.

Polynucleotides that may be introduced include those that confer or contribute to an altered trait such as altered amino acids, include for example, coding sequences for plant amino acid biosynthetic enzymes, coding sequences for plant tryptophan synthase, or coding sequences for methionine metabolic enzymes. Examples are described in U.S. Pat. Nos. 6,127,600, 5,990,389, 5,850,016, 5,885,802, 5,885,801 6,664,445 6,459,019 6,441,274 6,346,403, 5,939,599, 5,912, 414, 5,633,436, 5,559,223, the entire disclosures of which are herein incorporated by reference.

Polynucleotides that may be introduced include those that confer or contribute to an altered trait such as male sterility. For example coding sequences for a deacetylase gene, the use of stamen-specific promoters, barnase and barstar genes may be used. Examples are described in U.S. Pat. Nos. 5,432,068, 4,654,465, 4,727,219, 3,861,709, and 3,710,511, the disclosures of each of which are herein incorporated by reference in their entireties.

Polynucleotides that may be introduced include those that create a site for site specific DNA integration, such as the introduction of FRT sites that may be used in the FLP/FRT system and/or Lox sites that may be used in the Cre/Loxp system.

Polynucleotides that may be introduced include those that alter abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) See for example, U.S. Pat. Nos. 5,892,009, 5,965,705, 5,929,305, 5,891,859, 6,417,428, 6,664,446, 6,706,866, 6,717,034, 6,801,104, 6,084,153, 6,177,275, and 6,107,547, and US Patent Publication Nos. 20040128719, 20030166197 20040098764 and 20040078852. The disclosures of each of these documents are herein incorporated by reference in their entireties.

Polynucleotides that may be introduced include those that alter plant growth and agronomic traits such as yield, flowering, plant growth and/or plant structure. Examples are described in U.S. Pat. Nos. 6,573,430, 6,713,663 6,794,560, 6,307,126, the disclosures of each of which are herein incorporated by reference in their entireties.

It will be apparent to those of skill in the art that variations may be applied to the compositions and methods described herein and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

It is to be understood that the invention is not limited in its application to the details of construction and the arrangement of components set forth in the description. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The following non-limiting examples are purely illustrative.

EXAMPLES

Example 1

Disease Resistance of Cultivar and Cultivar Components

The response of Magnum Salt to various diseases was evaluated according to the "Standard Tests to Characterize Alfalfa Cultivars, 3$^{rd}$ edition, as amended July 1998", approved by the North American Alfalfa Improvement Conference. The resistance or susceptibility of the cultivar to bacterial wilt (*Clavibacter michiganense*), Fusarium wilt (*Fusarium oxysporum*), *Phytophthora* root rot (*Phytophthora megasperma*), *Verticillium* wilt (*Verticillium albo-atrum*), stem nematode (*Ditylenchus dipsaci*) and northern root-knot nematode (*Meloidogyne hapla*), anthracnose (*Colletotrichum trifolii*) (Race 1), *Aphanomyces* root rot (Race 1) (*Aphanomyces euteiches*), pea aphid (*Acyrthosipon pisum*), and southern root-knot nematode (*Meloidogyne incognita*) was assessed. For each disease tested, appropriate check cultivars, including resistant and susceptible cultivars, were employed as controls. The results are presented in Tables 1 through 10.

For each type of disease tested, each line of plants was assigned to one of five classes of resistance according to the percentage of resistant plants as follows:

| Class | % Resistant plants |
| --- | --- |
| Susceptible | <6 |
| Low resistant | 6-14 |
| Moderately resistant | 15-30 |
| Resistant | 31-50 |
| Highly resistant | >50 |

TABLE 1

Resistance to anthracnose (Race 1) disease (*Colletotrichum trifolii*)
Test conducted by Dairyland Research at Clinton, WI.

| Variety | Resistance Class | Year Tested | Syn Gen | Unadjusted % R | Adjusted % R |
| --- | --- | --- | --- | --- | --- |
| Magnum Salt | R | 2009 | 1 | 32 | 36 |
| 1. Saranac AR | R | | | 40 | 45 |
| 2. Saranac | S | | | 0 | 0 |
| Test Mean: | | | | 38 | 43 |
| L.S.D. (.05%) | | | | 17 | |
| C.V. (%) | | | | 19 | |

Note:
Unadjusted % R is the actual raw data summary.
Adjusted % R is transformed to the standards of the resistant check.

TABLE 2

Resistance to *Aphanomyces* Root Rot (Race 1) (*Aphanomyces euteiches*)
Test conducted by Dairyland Research at Clinton, WI.

| Variety | Resistance Class | Year Tested | Syn Gen | Unadjusted % R | Adjusted % R |
| --- | --- | --- | --- | --- | --- |
| Magnum Salt | R | 2009 | 1 | 35 | 36 |
| 1. WAPH-1 (Race 1) | R | | | 48 | 50 |
| 2. Saranac (Races 1 & 2) | S | | | 0 | 0 |
| Test Mean: | | | | 41 | 43 |
| L.S.D. (.05%) | | | | 24 | |
| C.V. (%) | | | | 19 | |

TABLE 3

Resistance to Bacterial Wilt Disease (*Clavibacter michiganense*)
Test conducted by Dairyland Research at Clinton, WI.

| Variety | Resistance Class | Year Tested | Syn Gen | Unadjusted % R | Adjusted % R |
| --- | --- | --- | --- | --- | --- |
| Magnum Salt | HR | 2009 | 1 | 83 | 70 |
| 1. Vernal | R | | | 50 | 42 |
| 2. Narragansett | S | | | 4 | 3 |
| Test Mean: | | | | 67 | 56 |
| L.S.D (.05%). | | | | 28 | |
| C.V. (%) | | | | 26 | |

TABLE 4

Resistance to *Fusarium* Wilt Disease (*Fusarium oxysporum*)
Test conducted by Dairyland Research at Clinton, WI.

| Variety | Resistance Class | Year Tested | Syn Gen | Unadjusted % R | Adjusted % R |
|---|---|---|---|---|---|
| Magnum Salt | HR | 2009 | 1 | 89 | 78 |
| 1. Agate | HR | | | 61 | 54 |
| 2. MNGN-1 | S | | | 5 | 4 |
| Test Mean: | | | | 88 | 78 |
| L.S.D. (.05%) | | | | 23 | |
| C.V. (%) | | | | 17 | |

TABLE 5

Resistance to *Phytophthora* Root Rot Disease (*Phytophthora medicaginis*)
Test conducted by Dairyland Research at Clinton, WI.

| Variety | Resistance Class | Year Tested | Syn Gen | Unadjusted % R | Adjusted % R |
|---|---|---|---|---|---|
| Magnum Salt | HR | 2009 | 1 | 53 | 56 |
| 1. WAPH-1 (seedling) | HR | | | 51 | 55 |
| 2. Saranac | S | | | 0 | 0 |
| Test Mean: | | | | 55 | 59 |
| L.S.D. (.05%) | | | | 28 | |
| C.V. (%) | | | | 21 | |

TABLE 6

Resistance to *Verticillium* Wilt Disease (*Verticillium albo-atrum*)
Test conducted by Dairyland Research at Clinton, WI.

| Variety | Resistance Class | Year Tested | Syn Gen | Unadjusted % R | Adjusted % R |
|---|---|---|---|---|---|
| Magnum Salt | HR | 2010 | 2 | 88 | 84 |
| 1. Oneida VR | HR | | | 63 | 60 |
| 2. Saranac | S | | | 5 | 5 |
| Test Mean: | | | | 69 | 66 |
| L.S.D. (.05%) | | | | 19 | |
| C.V. (%) | | | | 15 | |

TABLE 7

Resistance to Pea Aphid Insect (*Acyrthosipon pisum*)
Test conducted by Dairyland Research at Clinton, WI.

| Variety | Resistance Class | Year Tested | Syn Gen | Unadjusted % R | Adjusted % R |
|---|---|---|---|---|---|
| Magnum Salt | R | 2011 | 2 | 47 | 47 |
| 1. CUF 101 | HR | | | 55 | 55 |
| 2. Ranger | S | | | 10 | 10 |
| Test Mean: | | | | 40 | 40 |
| L.S.D. (.05%) | | | | 28 | |
| C.V. (%) | | | | 36 | |

TABLE 8

Resistance to Northern Root-Knot Nematode (*Meloidogyne hapla*)
Test conducted by Dairyland Research at Clinton, WI.

| Variety | Resistance Class | Year Tested | Syn Gen | Unadjusted % R | Adjusted % R |
|---|---|---|---|---|---|
| Magnum Salt | HR | 2010 | 2 | 64 | 63 |
| 1. Nevada Syn XX | HR | | | 91 | 90 |
| 2. Lahontan | S | | | 8 | 8 |
| Test Mean: | | | | 71 | 70 |
| L.S.D. (.05%) | | | | 15 | |
| C.V. (%) | | | | 13 | |

TABLE 9

Resistance to Southern Root-Knot Nematode (*Meloidogyne incognita*)
Test conducted by Dairyland Research at Clinton, WI.

| Variety | Resistance Class | Year Tested | Syn Gen | Unadjusted % R | Adjusted % R |
|---|---|---|---|---|---|
| Magnum Salt | R | 2010 | 2 | 61 | 52 |
| 1. Moapa 69 | R | | | 59 | 50 |
| 2. Lahontan | S | | | 5 | 4 |
| Test Mean: | | | | 52 | 44 |
| L.S.D. (.05%) | | | | 17 | |
| C.V. (%) | | | | 20 | |

TABLE 10

Resistance to Stem Nematode (*Ditylenchus dipsaci*)
Test conducted by Dairyland Research at Clinton, WI.

| Variety | Resistance Class | Year Tested | Syn Gen | Unadjusted % R | Adjusted % R |
|---|---|---|---|---|---|
| Magnum Salt | HR | 2010 | 2 | 67 | 56 |
| 1. Lahontan | R | | | 48 | 40 |
| 2. Ranger | S | | | 12 | 10 |
| Test Mean: | | | | 60 | 50 |
| L.S.D. (.05%) | | | | 22 | |
| C.V. (%) | | | | 22 | |

Example 2

Fall Dormancy

Magnum Salt is a moderately dormant variety similar to the fall dormancy 4 ("FD4") check. See Tables 11 and 12.

TABLE 11

Fall Dormancy
Fall dormancy as determined from spaced plantings relative to seven (7) standard check varieties.
Test conducted by Dairyland Research at Clinton, WI.
Score or Average Height

| Test Location | Syn Gen | Date Last Cut (Mo/Yr) | Date Measured (Mo/Yr) | Magnum Salt | Check Varieties | | | LSD .05 | CV % |
|---|---|---|---|---|---|---|---|---|---|
| | | | | | 1. 5246 (FD3) | 2. Legend (FD4) | 3. Archer (FD5) | | |
| Clinton, WI | F1 | September 2009 | October 2009 | 6.8 | 6.3 | 6.9 | 10.5 | 0.99 | 10.2 |
| | | | | | 4. Maverick 2.1 | 5. Vernal 4.2 | 6. ABI 700 12.6 | | |
| | | | | | 7. Doña Ana 14.7 | | | | |

Scoring system used: Fall growth in inches

TABLE 12

Fall Dormancy
Magnum Salt is most similar to the following fall dormancy class:

| Very Dormant | Dormant | Moderately Dormant | Non-Dormant | Very Non-Dormant |
|---|---|---|---|---|
| FD 1 ( ) | FD 2 ( ) FD 3 ( ) | FD 4 (X) FD 5 ( ) FD 6 ( ) | FD 7 ( ) FD 8 ( ) | FD 9 ( ) |

Example 3

Persistence Advantage of Magnum Salt

Magnum Salt shows similar persistence to Magnum VI and 54V46 when grown in the field, such as near Clinton, Wis., and a 36% and 87% better persistence than Magnum VI and 54V46 respectively, when grown in saline soils such as near Buffalo, N. Dak. See Table 13.

TABLE 13

Persistence
Tests conducted by Dairyland Research at Clinton, WI and Buffalo, ND.
% Stand

| Test Location | Syn Gen | Date Seeded Mo/Yr | # of Years Harvester | # of Harvests | Date of Readings (Mo/Yr) Initial--Final | Check Varieties | | | LSD .05 | CV % |
|---|---|---|---|---|---|---|---|---|---|---|
| | | | | | | Magnum Salt Initial/Final | Magnum VI Initial/Final | 54V46 Initial/Final | | |
| Clinton, WI | 1 | April 2009 | 3 | 11 | May 2009-October 2011 | 100/85 | 100/85 | 100/85 | 3 | 6.8 |
| Buffalo, ND | 1 | April 2009 | 3 | 5 | July 2009-October 2011 | 100/75 | 100/55 | 100/40 | 25 | 22 |

Example 4

Survival of Over Wintered Plants

Winter survival was determined from spaced plantings relative to standard check varieties. Tests conducted by Dairyland Research at Clinton, Wis. Check varieties were chosen so as to bracket the winter survival data of Magnum Salt. Data for check varieties in classes 1 through 6 were included. Magnum Salt is very winder hardy, with winter survival similar to the very hardy winter survival class 2. See Tables 14 and 15.

TABLE 14

Winter Survival
Winter Survival Rating

| Test Location | Syn Gen | Date Planted (Mo/Yr) | Date Measured (Mo/Yr) | Magnum Salt | 1 | 2 | 3 | 4 | 5 | 6 | LSD .05 | CV % |
|---|---|---|---|---|---|---|---|---|---|---|---|---|
| | | | | | | | Check Class | | | | | |
| Clinton, WI | 1 | April 2009 | May 2010 | 2.1 | 1.6 | 2.2 | 2.9 | 3.4 | 3.8 | 5.0 | .99 | 16.1 |
| Clinton, WI | 2 | April 2010 | May 2011 | 2.2 | 1.8 | 2.3 | 3.0 | 3.6 | 3.9 | 5.0 | 1.02 | 15.1 |

1 = ZG 9830;
2 = 5262;
3 = WL325HQ;
4 = G-2852;
5 = Archer;
6 = CUF101

TABLE 15

Winter Survival Classes

| 1 { } Extremely Winterhardy (X) ZG9830 | 2 {X} Very Winterhardy (X) 5262 | 3 { } Moderately Winterhardy (X) WL325HQ | 4 { } Low Winterhardy (X) G-2852 | 5 { } Winterhardy (X) Archer | 6 { } Non-Winterhardy (X) CUF 101 |
|---|---|---|---|---|---|

Example 5

Flower Color

Magnum Salt flower color was classified according to the USDA Agriculture Handbook No. 424-A System for Visually Classifying Alfalfa Flower Color. Flower color at full bloom in the Syn. 2 generation is 90% purple, 10% variegated with trace amounts of cream, white and yellow. See Table 16.

TABLE 16

Flower Color

| Color | Percent |
|---|---|
| Purple | 90% |
| Variegated | 10% |
| Cream | Trace |
| Yellow | Trace |
| White | Trace |

Example 6

Forage Yield

Forage yields of Magnum Salt were measured and are presented in Tables 17. Magnum Salt showed a forage yield performance expressing a 5% advantage over 17 popular conventional varieties across 106 harvests. See Table 17. Magnum Salt showed yield performance that is 16% better than four popular glyphosate (RR) herbicide tolerant alfalfa varieties across 8 harvests. See Table 17.

TABLE 17

Magnum Salt
Head to Head Forage Yield
Data collected across at various Midwest locations

| Variety | Total Tons | % Advantage | # of Harvests |
|---|---|---|---|
| Magnum VI | 158.1 | 105 | 106 |
| Competitor (aver) | 150.55 | | |

| Variety | Total Tons | % Advantage | # of Harvests | Variety | Total Tons | % Advantage | # of Harvests |
|---|---|---|---|---|---|---|---|
| Magnum Salt | 3.3 | 118 | 2 | Magnum Salt | 3.3 | 106 | 2 |
| 54Q32 | 2.8 | | | WL348AP | 3.1 | | |
| Magnum Salt | 3.3 | 110 | 2 | Magnum Salt | 48.9 | 105 | 35 |
| 55V48 | 3.0 | | | WL363AP | 46.76 | | |
| Magnum Salt | 17.4 | 102 | 13 | Magnum Salt | 3.3 | 106 | 2 |
| 55V12 | 17.13 | | | Forage Gold | 3.1 | | |
| Magnum Salt | 3.3 | 106 | 2 | Magnum Salt | 3.3 | 110 | 2 |
| Ameristand 407TQ | 3.1 | | | PGI557 | 3.0 | | |
| Magnum Salt | 3.3 | 114 | 2 | Magnum Salt | 3.3 | 110 | 2 |
| DKA43-13 | 2.9 | | | Consistency 4.1RR | 3.0 | | |
| Magnum Salt | 3.3 | 106 | 2 | Magnum Salt | 3.3 | 122 | 2 |
| Rebound 6 | 3.1 | | | V-45RR | 2.7 | | |
| Magnum Salt | 3.3 | 106 | 2 | Magnum Salt | 3.3 | 122 | 2 |
| 6422Q | 3.1 | | | LiberatorRR | 2.7 | | |
| Magnum Salt | 45.6 | 101 | 33 | Magnum Salt | 3.3 | 110 | 2 |
| Magnum VI | 44.96 | | | WL355RR | 3.0 | | |
| Magnum Salt | 3.3 | 106 | 2 | | | | |
| WL343HQ | 3.1 | | | | | | |

Example 7

Forage Production Under Salt Stress

Forage yields of Magnum Salt were measured under normal irrigation, and under salt stress conditions after being irrigated with 110 mM Na Cl. Seeds were sown in a peat, perlite, sand and organic potting mix (2:3:3:4 ratio). Plants were grown in a greenhouse under high light intensity and a 24 hour daylength. All plants received only non-saline irrigation for the first 14 days, thereafter half of the plants received 025× Hoagland solution containing 110 mM NaCl, applied so that the foliage was not wetted. Herbage was harvested 49-63 days post-planting and discarded; three additional harvests were made at 28-35 day intervals and fresh forage weight recorded for each plant. Containers were flushed with fresh water after each harvest followed by irrigation with the appropriate nutrient solutions. The salt/control (S/C) ratio was calculated for each variety as an estimate of salt-tolerance. The AZ-90NDC-ST tolerant control gave an S/C ratio of 0.613, within the 0.6 to 0.75 range typically found for control cultivars. Magnum Salt gave an S/C ration of 0.611, very similar to the tolerant control and higher than the susceptible control, AZ-88NDC (0.507) and alfalfa variety HybriForce-2420/Wet (0.489). The data are presented in Table 18.

TABLE 18

Magnum Salt
Forage Yield under Salt Stress

| | Mean total yield of surviving plants over three harvests (g/plant)* when irrigated with: | | |
|---|---|---|---|
| Plant Variety | 110 mM NaCl | Control | S/C fraction |
| Magnum Salt | 3.059 | 5.006 | 0.611 |
| HybriForce-2420/Wet | 3.038 | 6.210 | 0.489 |
| AZ-90NDC-ST (Salt Tolerant control) | 3.512 | 5.730 | 0.613 |
| AZ-88NDC (Salt Susceptible control) | 3.131 | 6.176 | 0.507 |
| LSD (.05) | | | .091 |
| CV(%) | | | 14.32 |

What is claimed is:

1. A *Medicago sativa* seed designated as Magnum Salt, wherein a sample of said seed has been deposited as ATCC Accession Number PTA-13036.

2. A plant, or a part thereof, produced by growing the seed of claim 1.

3. A pollen from the plant of claim 2.

4. An ovule from the plant of claim 2.

5. An alfalfa plant having all the physiological and morphological characteristics of the plant of claim 2.

6. A tissue culture of regenerable cells from the plant, or the part thereof, of claim 2.

7. The tissue culture of regenerable cells of claim 6, wherein the regenerable cells are selected from the group consisting of protoplasts and calli, and wherein the regenerable cells are from a leaf, pollen, ovule, cotyledon, hypocotyl, embryo, root, pod, flower, shoot or stalk.

8. A protoplast produced from the tissue culture of claim 6.

9. The tissue culture of claim 6, wherein the culture is a callus culture.

10. An alfalfa plant regenerated from the tissue culture of claim 6, wherein the plant has all of the physiological and morphological characteristics of a plant produced by growing a seed designated Magnum Salt and deposited under ATCC Accession No. PTA-13036.

11. A tissue culture of regenerable cells from the plant, or the part thereof, of claim 5.

12. The tissue culture of claim 11, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

13. A protoplast produced from the tissue culture of claim 11.

14. The tissue culture of claim 11, wherein the culture is a callus culture.

15. An alfalfa plant regenerated from the tissue culture of claim 11, wherein the plant has all of the physiological and morphological characteristics of a plant produced by growing a seed designated Magnum Salt and deposited under ATCC Accession No. PTA-13036.

16. A method for producing an alfalfa cultivar Magnum Salt-derived alfalfa plant, comprising: (a) crossing Magnum Salt plants grown from Magnum Salt seed, representative seed of which has been deposited under ATCC Accession No: PTA-13036, with a second alfalfa plant to yield progeny alfalfa seed; and (b) growing the progeny seed to yield an alfalfa cultivar Magnum Salt-derived alfalfa plant.

17. The method of claim 16, further comprising: (c) crossing the alfalfa cultivar Magnum Salt-derived alfalfa plant of (b) with itself or a third alfalfa plant to yield a second alfalfa Magnum Salt-derived alfalfa progeny seed; and (d) growing the second alfalfa progeny seed of (c) to yield a second alfalfa cultivar Magnum Salt-derived alfalfa plant.

18. The method of claim 17, wherein (c) and (d) are repeated at least one time to generate an additional alfalfa cultivar Magnum Salt-derived alfalfa plant.

19. A method of introducing a desired trait into alfalfa Magnum Salt comprising:
(a) crossing Magnum Salt plants grown from Magnum Salt seed, representative seed of which has been deposited under ATCC Accession No: PTA-13036, with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates;
(b) selecting F1 progeny plants that have the desired trait to produce selected F1 progeny plants;
(c) crossing the selected progeny plants with the Magnum Salt plants to produce backcross progeny plants; (d) selecting for backcross progeny plants that have the desired trait and physiological and morphological characteristics of alfalfa variety Magnum Salt to produce selected backcross progeny plants; and
(e) repeating steps (c) and (d) three or more times in succession to produce selected fourth or higher backcross progeny plants that comprise the desired trait and all the physiological and morphological characteristics of alfalfa variety Magnum Salt.

20. A plant produced by the method of claim 19, wherein the plant has the desired trait and all of the physiological and all morphological characteristics of said alfalfa variety Magnum Salt.

21. A method for producing an alfalfa plant having an altered agronomic trait comprising introducing a polynucleotide into a Magnum Salt plant grown from Magnum Salt seed, representative seed of which has been deposited under ATCC Accession No: PTA-13036, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

22. An alfalfa plant produced by the method of claim 21, wherein the plant has the altered agronomic trait and all of the physiological and all morphological characteristics of said alfalfa variety Magnum Salt.

\* \* \* \* \*